US006214841B1

(12) United States Patent
Jackson et al.

(10) Patent No.: US 6,214,841 B1
(45) Date of Patent: Apr. 10, 2001

(54) ANTITHROMBOTIC COMPOUND

(75) Inventors: Charles Van Jackson; Kenneth Dean Kurz, both of Indianapolis, IN (US); Robert Theodore Shuman, Sedona, AZ (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/423,453

(22) PCT Filed: May 7, 1998

(86) PCT No.: PCT/US98/09311

§ 371 Date: Nov. 8, 1999

§ 102(e) Date: Nov. 8, 1999

(87) PCT Pub. No.: WO98/51684

PCT Pub. Date: Nov. 19, 1998

Related U.S. Application Data

(60) Provisional application No. 60/046,584, filed on May 15, 1997.

(51) Int. Cl.[7] ...................... C07D 401/06; A61K 31/395; A61K 31/47
(52) U.S. Cl. ................... 514/310; 514/210.18; 546/146; 540/354
(58) Field of Search ........................... 546/146; 540/354; 514/210.18, 310

(56) References Cited

U.S. PATENT DOCUMENTS

| 5,252,566 | 10/1993 | Shuman .............................. 514/210 |
| 5,416,093 | 5/1995 | Shuman .............................. 514/307 |
| 5,430,023 | 7/1995 | Gesellchen et al. ................... 514/18 |
| 5,436,229 | 7/1995 | Ruterbories et al. .................. 514/18 |
| 5,523,308 | 6/1996 | Constanzo et al. .................. 514/317 |
| 5,599,793 | 2/1997 | Chirgadze et al. ..................... 514/18 |

FOREIGN PATENT DOCUMENTS

| 0 479 489 A2 | 4/1992 | (EP) . |
| 0 504 064 A1 | 9/1992 | (EP) . |
| 0 542 525 A2 | 5/1993 | (EP) . |
| 0 672 658 A1 | 9/1995 | (EP) . |
| 8-20597 | 1/1996 | (JP) . |
| WO 96/30396 | 10/1996 | (WO) . |
| WO 96/37496 | 11/1996 | (WO) . |
| WO 96/40741 | 12/1996 | (WO) . |
| WO 96/40742 | 12/1996 | (WO) . |
| WO 96/40744 | 12/1996 | (WO) . |
| WO 97/12904 | 4/1997 | (WO) . |
| WO 97/17363 | 5/1997 | (WO) . |
| WO 97/30073 | 8/1997 | (WO) . |
| WO 97/31937 | 9/1997 | (WO) . |
| WO 97/31939 | 9/1997 | (WO) . |
| WO 97/47687 | 12/1997 | (WO) . |
| WO 97/48706 | 12/1997 | (WO) . |

OTHER PUBLICATIONS

Costanzo, M.J., Maryanoff, B.E., Hecker, L.R., Schott, M.R., Yabut, S.C., Zhang, H,.C., Andrade–Gordon, P, Kauffman, J.A., Lewis, J.M., Krishnan, Rl., and Tulinsky, A. Potent Thrombin Inhibitors That Probe the $S_1'$ Subsite: Tripeptide Transition State Analogues Based on a Heterocycle–Activated Carbonyl Group. J.Med. Chem. 1996, 39, 3039–3043.

*Primary Examiner*—Zinna Northington Davis
(74) *Attorney, Agent, or Firm*—Thomas E. Jackson

(57) ABSTRACT

This application relates to a novel compound of formula (I) (or a pharmaceutically acceptable salt thereof) as defined herein, processes and Intermediates for its preparation, pharmaceutical formulations comprising the novel compound of formula (I), and the use of the compound of formula (I) as an antithrombotic agent.

13 Claims, No Drawings

ANTITHROMBOTIC COMPOUND

This application is a 371 of PCT/US98/09311 filed May 7, 1998 which claims the benefit of U.S. Provisional Application No. 60/046,584, filed May 15, 1997.

This invention relates to a heterocyclic ketone compound having surprisingly potent antithrombotic efficacy. Thus, the invention relates to the new antithrombotic compound, pharmaceutical compositions containing the compound as an active ingredient, and the use of the compound for prophylaxis or treatment of a thromboembolic disorder such as venous thrombosis, pulmonary embolism, arterial thrombosis, in particular myocardial ischemia, myocardial infarction or cerebral thrombosis, general hypercoagulable states and local hypercoagulable states, such as following angioplasty and coronary bypass operations, or generalized tissue injury as it relates to the inflammatory process. In addition, the new compound is useful as an anticoagulant in in vitro and ex vivo applications.

Certain peptidyl heterocycles are disclosed in U.S. Pat. No. 5,523,308 as inhibitors of thrombin useful in the treatment of thrombin-related disorders. Surprisingly, the compound of the instant invention exhibits high potency in inhibition of both thrombin and factor Xa, as well as highly potent antithrombotic efficacy.

According to the invention, there is provided a compound of formula I

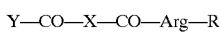

wherein
  Arg is L-arginyl;
  R is 2-benzothiazolyl;
  X—CO— is L-prolyl or (S)-azetidin-2-carbonyl; and
  Y—CO— is a group of formula IIa, IIb, IIc or IId;

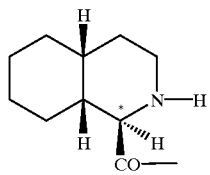

IIa

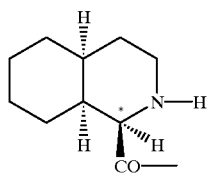

IIb

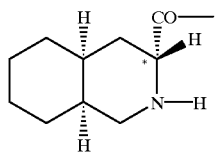

IIc

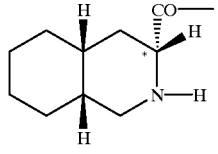

IId or a pharmaceutically acceptable salt thereof.

A particular compound of formula I is one in which X—CO— is L-prolyl (Pro).

A more particular compound of formula I is one in which X—CO— is Pro and Y—CO— is a group of formula IIa or IIb.

One preferred compound of formula I is one in which X—CO— is Pro and Y—CO— is a group of formula IIa, which compound may be denoted as a compound of formula Ia.

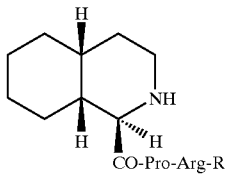

Ia

The preferred species is described hereinbelow as Example 1, where it is isolated as the acid addition salt with sulfuric acid.

Another particular compound of formula I is one in which X—CO— is Pro and Y—CO— is a group of formula IIb, which compound may be denoted as a compound of formula Ib.

In addition to a compound of formula I, the present invention provides a pharmaceutical composition comprising a compound of formula I, or a pharmaceutically acceptable salt thereof, in association with a pharmaceutically acceptable carrier, diluent or excipient.

The present invention also provides a method of inhibiting thrombosis in a mammal comprising administering to a mammal in need of treatment, an antithrombotic dose of a compound of formula I.

As is further discussed below, a compound of the instant invention is a potent, direct inhibitor of one or both of the enzymes thrombin and factor Xa of the coagulation cascade. Accordingly, the present invention further provides a method of inhibiting thrombin comprising administering to a mammal in need of treatment, a thrombin inhibiting dose of a compound of formula I, as well as a method of inhibiting thrombin in an in vitro or ex vivo application. Similarly, the present invention further provides a method of inhibiting factor Xa comprising administering to a mammal in need thereof, a factor Xa inhibiting dose of a compound of formula I, as well as a method of inhibiting factor Xa in an in vitro or ex vivo application.

It is preferred that the chiral center indicated by the asterisk in the group Y be of (R)-stereochemistry, corresponding to that of a D-amino acid.

However, it is to be understood that the present invention encompasses a compound of formula I as a mixture of diastereomers, as well as in the form of an individual diastereomer, and that the present invention encompasses a compound of formula I as a mixture of enantiomers, as well as in the form of an individual enantiomer, any of which mixtures or form possesses antithrombotic properties, it being well known in the art how to prepare or isolate particular forms and how to determine antithrombotic properties by standard tests including those described below. Owing to the facile epimerization of the α-proton of the Arg moiety, adjacent to the benzoxazolyl keto group, it may be preferred to use the compound of formula I as a mixture of epimers at that center.

In addition, a compound of formula I (or a pharmaceutically acceptable salt thereof) may form a solvate with water or an organic solvent. Further, the compound, salt or solvate thereof may exhibit polymorphism. The present invention also encompasses any such solvate, polymorphic form, or mixture thereof.

A compound of formula I may be made by processes which include processes known in the chemical art for the production of structurally analogous compounds or by a novel process described herein. Novel processes and intermediates for the manufacture of a compound of formula I as defined above provide further feature of the invention and are illustrated by the following procedures in which the meanings of the generic radicals are as defined above, unless otherwise specified. It will be recognized that it may be preferred or necessary to prepare a compound of formula I in which a functional group is protected using a conventional protecting group, then to remove the protecting group to provide the compound of formula I.

Thus, there is provided a process for preparing a compound of formula I (or a pharmaceutically acceptable salt thereof) as provided in any of the above descriptions which includes oxidation of the alcohol of a corresponding compound of formula III

   III in which Arg(OH) indicates that the carbonyl portion of the L-arginyl group is replaced by a hydroxymethylene group;

whereafter, for any of the above procedures, when a functional group is protected using a protecting group, removing the protecting group; and whereafter, for any of the above procedures, when a pharmaceutically acceptable salt of a compound of formula I is required, it is obtained by reacting the basic form of the compound of formula I with an acid affording a physiologically acceptable counterion or by any other conventional procedure, such as, for example, exchanging the counterion of a salt.

Conveniently, the oxidation is carried out in an inert solvent, using oxalyl chloride, dimethyl sulfoxide and a tertiary amine, for example as described below in Example 1. It generally is preferred that the amino groups of Y—CO— and the Arg side chain be protected during the oxidation.

A compound corresponding to compound of formula I in which one or more functional groups is protected provides another aspect of the invention. Such a compound may be represented as a compound of Formula Ip (PY)Y—CO—X—CO—Arg(p$^A$)—R   Ip which bears one or more of the protecting groups p$^A$ and P$^Y$ wherein p$^A$ is an optional protecting group(s) for the guanidino moiety of the Arg side chain and P$^Y$ is an optional protecting group for the amino nitrogen of the perhydroisoquinoline moiety. A typical value for p$^A$ is tosyl and for P$^Y$ is benzyloxycarbonyl.

Conveniently, an alcohol of formula III is prepared in a protected form by coupling a protected form of an acid of formula IV

Y—CO—X—CO—OH   IV with a protected form of the alcohol of formula V

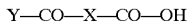   V using a conventional coupling method, for example the mixed anhydride method described in Example 1.

The (optionally protected) acid of formula IV may be made by a conventional method. For example, when Y—CO— is of formula IIa and X—CO— is prolyl, the protected acid of formula IV may be prepared as described below in Example 1 or as described in EP 670310 at Example 85. Similarly, when Y—CO— is of formula IId or IIb and X—CO— is prolyl, the protected acid of formula IV is disclosed at Example 80 or 82 of EP 670310 or U.S. Pat. No. 5,436,229. The preparation of the amino alcohol of formula V in which the guanidino group bears an N-tosyl protecting group is described below in Example 1.

As mentioned above, the invention includes a pharmaceutically acceptable salt of a compound of formula I, which possesses sufficiently basic functional groups to react with any of a number of inorganic and organic acids which afford a nontoxic anion to form a pharmaceutically acceptable salt. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

A compound of formula I is isolated best in the form of an acid addition salt. A salt of the compound of formula I formed with an acid such as one of those mentioned above is useful as a pharmaceutically acceptable salt for administration of the antithrombotic compound and for preparation of a formulation of the compound. Other acid addition salts may be prepared and used in the isolation and purification of the compound.

The compound of formula I is believed to selectively inhibit thrombin and factor Xa over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in mammals comprising administering to a mammal in need of treatment an effective (coagulation inhibiting) dose of a compound of formula I.

The coagulation inhibition and thromboembolic disorder treatment contemplated by the present method includes both medical therapeutic and/or prophylactic treatment as appropriate.

In a further embodiment the invention relates to treatment, in a human or animal, of conditions where inhibition of thrombin or factor Xa is required. The compound of the invention is expected to be useful in mammals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compound has a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compound has expected utility in the treatment or prophylaxis of atherosclerotic disorders (diseases) such as coronary arterial disease, cerebral arterial disease and peripheral arterial disease. Further, the compound is expected to be useful together with thrombolytics in myocardial infarction. Further, the compound has expected utility in prophylaxis for reocclusion after thrombolysis, percutaneous transluminal angioplasty (PTCA) and coronary bypass operations. Further, the compound has expected utility in prevention of rethrombosis after microsurgery. Further, the compound is expected to be useful in anticoagulant treatment in connection with artificial organs and cardiac valves. Further, the compound has expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compound has expected utility in other diseases where blood coagulation could be a fundamental contributing process or a source of secondary pathology, such as cancer, including metastasis, inflammatory diseases, including arthritis, and diabetes. The anti-coagulant compound is administered orally, parenterally e.g. by intravenous infusion (iv), intramuscular injection (im), subcutaneously (sc), or transdermally.

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to. its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides pharmaceutical compositions for use in the above described therapeutic method. Pharmaceutical compositions of the invention comprise an effective antithrombotic amount of a compound of formula I in association with a pharmaceutically acceptable carrier, excipient or diluent. For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9 percent), 5 percent dextrose, Ringer's solution and the like. For transdermal administration the antithrombotic is formulated in a patch.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The antithrombotic compound can be administered by a variety of routes including oral, rectal, transdermal, subcutaneous, intravenous, intramuscular, and intranasal. The compound of the present invention preferably is formulated prior to administration. Another embodiment of the present invention is a pharmaceutical composition comprising an effective amount of a compound of formula I or a pharmaceutically acceptable salt or solvate thereof in association with a pharmaceutically acceptable carrier, diluent or excipient therefor.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

The present pharmaceutical compositions are prepared by known procedures using well known and readily available ingredients. The compositions of this invention may be formulated so as to provide quick, sustained, or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to formula I or a pharmaceutically acceptable salt or solvate thereof.

Formulation 1: Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2: A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3: An aerosol solution is prepared containing the following components:

|  | Weight |
| --- | --- |
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to 30° C. and transferred to a filling device. The required amount is then fed to a stainless steel container and diluted with the remainder of the propellant. The valve units are then fitted to the container.

Formulation 4: Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |

-continued

Formulation 4: Tablets, each containing 60 mg of active ingredient, are made as follows:

| Magnesium stearate | 0.5 mg |
| --- | --- |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5: Capsules, each containing 80 mg of active ingredient, are made as follows:

| Active ingredient | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6: Suppositories, each containing 225 mg of active ingredient, are made as follows:

| Active ingredient | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7: Suspensions, each containing 50 mg of active ingredient per 5 mL dose, are made as follows:

| Active ingredient | 50 mg |
| --- | --- |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8: An intravenous formulation may be prepared as follows:

| | |
|---|---|
| Active ingredient | 100 mg |
| Isotonic saline | 1,000 mL |

The solution of the above ingredients generally is administered intravenously to a subject at a rate of 1 mL per minute.

The ability of a compound of the present invention to be an effective and orally active antithrombotic agent is evaluated in one or more of the following assays.

The compound provided by the invention (formula I) selectively inhibits the action of thrombin and/or factor Xa in mammals. The inhibition is demonstrated by in vitro inhibition of the amidase activity of the enzyme as measured in an assay in which the enzyme hydrolyzes a chromogenic substrate. For example, thrombin hydrolyzes N-benzoyl-L-phenylalanyl-L-valyl-L-arginyl-p-nitroanilide, N-benzoyl-L-Phe-L-Val-L-Arg-p-nitroanilide.

The assay is carried out by mixing 50 µL buffer (0.03M Tris, 0.15M NaCl, pH 7.4) with 25 µL of human thrombin solution (purified human thrombin, Enzyme Research Laboratories, South Bend, Indiana, at 8 NIH units/mL) and 25 µL of test compound in a solvent (50% aqueous methanol (v:v)). Then 150 µL of an aqueous solution of the chromogenic substate (at 0.25 mg/mL) are added and the rates of hydrolysis of the substrate are measured by monitoring the reactions at 405 nm for the release of p-nitroaniline. Standard curves are constructed by plotting free thrombin concentration against hydrolysis rate. The hydrolysis rates observed with test compounds are then converted to "free thrombin" values in the respective assays by use of the standard curves. The bound thrombin (bound to test compound) is calculated by subtracting the amount of free thrombin observed in each assay from the known initial amount of thrombin used in the assay. The amount of free inhibitor in each assay is calculated by subtracting the number of moles of bound thrombin from the number of moles of added inhibitor (test compound).

The Kass value is the hypothetical equilibrium constant for the reaction between thrombin and the test compound (I).

Thrombin + I ⇌ Thrombin-I

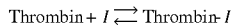

$$\text{Kass} = \frac{[\text{Thrombin-}I]}{[(\text{Thrombin}) \times (I)]}$$

Kass is calculated for a range of concentrations of test compounds and the mean value reported in units of liter per mole.

By substantially following the procedures described above for human thrombin, and using other human blood coagulation system serine proteases and using fibrinolytic system serine proteases, with the appropriate chromogenic substrates, identified below, the selectivity of the compounds of the present invention with respect to the coagulation factor serine proteases and to the fibronolytic serine proteases are evaluated as well as their substantial lack of interference with human plasma clot fibrinolysis.

Human factors X, Xa, IXa, XIa, and XIIa are purchased from Enzyme Research Laboratories, South Bend, Indiana; human urokinase from Leo Pharmaceuticals, Denmark; and recombinant activated Protein C (aPC) is prepared at Eli Lilly and Co. substantially according to U.S. Pat. No. 4,981,952. Chromogenic substrates: N-Benzoyl-Ile-Glu-Gly-Arg-p-nitroanilide (for factor Xa); N-Cbz-D-Arg-Gly-Arg-p-nitroanilide (for factor IXa assay as the factor Xa substrate); Pyroglutamyl-Pro-Arg-p-nitroanilide (for Factor XIa and for aPC); H-D-Pro-Phe-Arg-p-nitroanilide (for factor XIIa); and Pyroglutamyl-Gly-Arg-p-nitroanilide (for urokinase); are purchased from Kabi Vitrum, Stockholm, Sweden, or from Midwest Biotech, Fishers, Ind. Bovine trypsin is purchased from Worthington Biochemicals, Freehold, N.J., and human plasma kallikrein from Kabi Vitrum, Stockholm, Sweden. Chromogenic substrate H-D-Pro-Phe-Arg-p-nitroanilide for plasma kallikrein is purchased from Kabi Vitrum, Stockholm, Sweden. N-Benzoyl-Phe-Val-Arg-p-nitroanilide, the substrate for human thrombin and for trypsin, is synthesized according to procedures described above for the compounds of the present invention, using known methods of peptide coupling from commercially available reactants, or purchased from Midwest Biotech, Fishers, Ind.

Human plasmin is purchased from Boehringer Mannheim, Indianapolis, Ind.; nt-PA is purchased as single chain activity reference from American Diagnostica, Greenwich, Connecticut; modified-t-PA6 (mt-PA6) is prepared at Eli Lilly and Company by procedure known in the art (See, Burck, et al., *J. Biol. Chem.*, 265, 5120–5177 (1990). Plasmin chromogenic substrate H-D-Val-Leu-Lys-p-nitroanilide and tissue plasminogen activator (t-PA) substrate H-D-Ile-Pro-Arg-p-nitroanilide are purchased from Kabi Vitrum, Stockholm, Sweden.

In the chromogenic substrates described above the three-letter symbols Ile, Glu, Gly, Pro, Arg, Phe, Val, Leu and Lys are used to indicate the corresponding amino acid group isoleucine, glutamic acid, glycine, proline, arginine, phenylalanine, valine, leucine and lysine, respectively.

The antithrombotic compound preferably should spare fibrinolysis induced by urokinase, tissue plasminogen activator (t-PA) and steptokinase. This would be important to the therapeutic use of such agents as an adjunct to streptokinase, t-PA or urokinase thrombolytic therapy and to the use of such agents as an endogenous fibrinolysis-sparing (with respect to t-PA and urokinase) antithrombotic agents. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Butler Farms, Clyde, N.Y., U.S.A.) by venipuncture into 3.8 percent citrate. Fibrinogen is prepared from fresh dog plasma and human fibrinogen is prepared from in-date ACD human blood at the fraction I-2 according to previous procedures and specifications. Smith, *Biochem. J.*, 185, 1–11 (1980); and Smith, et al., *Biochemistry*, 11, 2958–2967, (1972). Human fibrinogen (98 percent pure/ plasmin free) is from American Diagnostica, Greenwich, Connecticut. Radiolabeling of fibrinogen I-2 preparations is performed as previously reported. Smith, et al., *Biochemistry*, 11, 2958–2967, (1972). Urokinase is purchased form Leo Pharmaceuticals, Denmark, as 2200 Ploug units/vial. Streptokinase is purchased from Hoechst-Roussel Pharmaceuticals, Somerville, N.J.

Methods
Effects on Lysis of Human Plasma Clots by t-PA

Human plasma clots are formed in micro test tubes by adding 50 µL thrombin (73 NIH unit/mL) to 100 µL human plasma which contains 0.0229 µCi 125-iodine labeled fibrinogen. Clot lysis is studied by overlaying the clots with 50 µL of urokinase or streptokinase (50, 100, or 1000 unit/mL) and incubating for 20 hours at room temperature. After incubation the tubes are centrifuged in a Beckman Microfuge. 25 µL 1 of supernate is added into 1.0 mL volume of 0.03 M tris/0.15 M NaCl buffer for gamma counting. Counting controls 100 percent lysis are obtained by omitting thrombin (and substituting buffer). The antithrombotic compound is evaluated for possible interference with fibrinolysis by including the compounds in the overlay solutions at 1, 5, and 10 µg/mL concentrations. Rough approximations of $IC_{50}$ values are estimated by linear extrapolations from data points to a value which would represent 50 percent of lysis for that particular concentration of fibrinolytic agent.

ANTICOAGULANT ACTIVITY

Materials

Dog plasma and rat plasma are obtained from conscious mixed-breed hounds (either sex, Butler Farms, Clyde, N.Y., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1–11 (1980); and Smith, et al., *Biochemistry*, 11, 2958–2967 (1972). Human fibrinogen is also purchased as 98 percent pure/plasmin free from American Diagnostica, Greenwich, Conn. Coagulation reagents ACTIN, Thromboplastin, and Human plasma are from Baxter Healthcare Corp., Dade Division, Miami, Fla. Bovine thrombin from Parke-Davis (Detroit, Mich.) is used for coagulation assays in plasma.

Methods
Anticoagulation Determinations

Coagulation assay procedures are as previously described. Smith, et al., *Thrombosis Research*, 50, 163–174 (1988). A CoAScreener coagulation instrument (American LABor, Inc.) is used for all coagulation assay measurements. The thrombin time (TT) is measured by adding 0.05 mL saline and 0.05 mL thrombin (10 NIH units/mL) to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02 M). The prothrombin time (PT) is measured by adding 0.05 mL saline and 0.05 mL Thromboplastin-C reagent to 0.05 mL test plasma. The compounds of formula I are added to human or animal plasma over a wide range of concentrations to determine prolongation effects on the TT, APTT and PT assays. Linear extrapolations are performed to estimate the concentrations required to double the clotting time for each assay.

Animals

Male Sprague Dawley rats (350–425 g, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous Shunt Model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol*, 77:29, 1982).

$FeCl_3$ Model of Arterial Injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. $FeCl_3$ hexahydrate is dissolved in water and the concentration (20 percent) is expressed in terms of the actual weight of $FeCl_3$ only. To injure the artery and induce thrombosis, 2.85 µL is pipetted into the cuff to bathe the artery above the thermocouple probe. Arterial occlusion is indicated by a rapid drop in temperature. The time to occlusion is reported in minutes and represents the elapsed time between application of $FeCl_3$ and the rapid drop in vessel temperature (see K. D. Kurz, *Thromb. Res.*, 60:269,1990).

Arterio-Venous (AV) Shunt Model in the Rabbit

Efficacy and potency of a compound are studied in a model of thrombosis in the anesthetized rabbit in which blood is shunted from the carotid artery through tubing to the left jugular vein. The shunt houses a thread upon which thrombotic material is deposited and is quantified in the presence and absence of a test compound. Specifically, the left jugular vein and right carotid artery are cannulated (PE 200 tubing, 22 cm). The tip of the arterial tubing is advanced approximately 1 cm and the tip of the venous tubing is advanced approximately 1 cm. The arterial and venous shunt segments are friction fitted into a center section of larger tubing (PE 260, 6 cm) with 4 strands of cotton thread (5.5 cm each), knotted together with a single knot at the end, in the lumen. Blood is circulated through the shunt for 15 min. The arterial and venous segments are clamped, the center section is detached, held vertically and the thread is carefully removed and weighed. The weight of a wet thread (38 mg, average of 10–4-stranded identical lengths) is subtracted from the total weight of the thread and thrombus. A drug is infused through a second catheter in the right jugular vein (2 cm inside vessel) starting 15 min before and throughout the 15 min period of blood circulation through the shunt. Another catheter, for sampling blood also is implanted in the right jugular and the tip is advanced 15 cm to ensure it is distal to the heart such that the sample is not enriched with blood flowing past the tip of the drug infusion catheter.

Spontaneous Thrombolysis Model

In vitro data suggests that peptide thrombin or factor Xa inhibitors at higher concentration may inhibit other serine proteases, such as plasmin and tissue plasminogen activator. To assess if a compound inhibits fibrinolysis in vivo, the rate of spontaneous thrombolysis is determined by implanting a labeled whole blood clot into the pulmonary circulation. Rat blood (1 mL) is mixed rapidly with bovine thrombin (4 IU, Parke Davis) and $^{125}I$ human Fibrogen (5 µCi, ICN), immediately drawn into silastic tubing and incubated at 37° C. for 1 hour. The aged thrombus is expelled from the tubing, cut into 1 cm segments, washed 3× in normal saline and each segment is counted in a gamma counter. A segment with known counts is aspirated into a catheter that is subsequently implanted into the jugular vein. The catheter tip is advanced to the vicinity of the right atrium and the clot is expelled to float into the pulmonary circulation. One hour after implant, the heart and lungs are harvested and counted separately. Thrombolysis is expressed as a percentage where:

$$\% \text{ Thrombolysis} = \frac{(\text{injected } cpm - \text{lung } cpm)}{\text{injected } cpm} \times 100$$

The fibrinolytic dissolution of the implanted clot occurs time-dependently (see J. P. Clozel, *Cardiovas. Pharmacol.*, 12:520, 1988).

Coagulation Parameters

Plasma thrombin time (TT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma is mixed with saline and human thrombin at 37° C. For.APTT, plasma (0.1 mL) and APTT solution (0.1 mL, Organon Teknika) are incubated for 5 minutes (37° C.) and $CaCl_2$ (0.1 mL, 0.025 M) is added to start coagulation. Assays are done in duplicate and averaged.

Index of Bioavailability

A measure of bioactivity, plasma thrombin time (TT), serves as a substitute for the assay of parent compound on the assumption that increments in TT resulted from thrombin inhibition by parent only. The time course of the effect of the thrombin inhibitor upon TT is determined after i.v bolus administration to anesthetized rats and after oral treatment of fasted conscious rats. Due to limitations of blood volume and the number of points required to determine the time course from time of treatment to the time when the response returns to pretreatment values, two populations of rats are used. Each sample population represents alternating sequential time points. The average TT over the time course is used to calculate area under the curve (AUC). The index of bioavailability is calculated by the formula shown below and is expressed as percent relative activity.

The area under the curve (AUC) of the plasma TT time course is determined and adjusted for the dose. This index of bioavailability is termed "% Relative Activity" and is calculated as $$\% \text{ Relative Activity} = \frac{AUC\ po}{AUC\ iv} \times \frac{Dose\ iv}{Dose\ po} \times 100$$

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the $FeCl_3$ model of arterial injury and in the spontaneous thrombolysis model. Bolus injection volume is 1 mL/kg for i.v., and 5 mL/kg for p.o. and infusion volume is 3 mL/hr.

Statistics

Results are expressed as means+/−SEM. One-way analysis of variance is used to detect statistically significant differences and then Dunnett's test is applied to determine which means are different. Significance level for rejection of the null hypothesis of equal means is P<0.05.

Animals

Male dogs (Beagles; 18 months—2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66–74° F.; 45–50 percent relative humidity; and lighted from 0600–1800 hours.

Pharmacokinetic Model

Test compound is formulated immediately prior to dosing by dissolving in sterile 0.9 percent saline to a 5 mg/mL preparation. Dogs are given a single 2 mg/kg dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are analyzed by HPLC MS. Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound of Tmax, Cmax; plasma half-life, t0.5; and area under the curve, A.U.C.; fraction of test compound absorbed, F.

Canine Model of Coronary Artery Thrombosis

Surgical preparation and instrumentation of the dogs are as described in Jackson, et al., *Circulation*, 82, 930–940 (1990). Mixed-breed hounds (aged 6–7 months, either sex, Butler Farms, Clyde, N.Y., U.S.A.) are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50 percent inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100-μA direct current (DC) to the anode. The current is maintained for 60 min and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.25, 0.5 and 1 mg/kg/hour is begun simultaneously with an infusion of thrombolytic agent (e.g. tissue plasminogen activator, streptokinase, APSAC). Reperfusion is followed for 3 hour after administration of test compound. Reocclusion of coronary arteries after successful thrombolysis is defined as zero CBF which persisted for at least 30 minutes.

Hematology and Template Bleeding Time Determinations

Whole blood cell counts, hemoglobin, and hematocrit values are determined on a 40-µL sample of citrated (3.8 percent) blood (1 part citrate:9 parts blood) with a hematology analyzer (Cell-Dyn 900, Sequoia-Turner. Mount View, Calif., U.S.A.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of $p<0.05$. All values are mean±SEM. All studies are conducted in accordance with the guiding principles of the American Physiological Society. Further details regarding the procedures are described in Jackson, et al., *J. Cardiovasc. Pharmacol.*, 21, 587–599 (1993).

The compound of formula Ia has particularly surprising properties. Thus, as DL-Arg-Ia (an approximately equal mixture of epimers at the Arg center, see Example 1, below), the compound demonstrated similar high potency as an inhibitor of thrombin (Kass=352 million, average of 3 assays) and of factor Xa (Kass=301 million, average of 3 assays). Moreover, highly potent antithrombotic efficacy was shown in the rabbit AV shunt model where an ED50% (infusion dose to reduce thrombus weight by 50%) value of 0.008 mg/kg/h i.v. was observed. At this dose, there was no observed change in the thrombin time ratio.

The following Examples are provided to further describe the invention and are not to be construed as limitations thereof. The abbreviations used in the examples have the following meanings.

Amino acids: Azt=azetidine-2-carboxylic acid,
Pro=proline
Anal.=elemental analysis
Boc=t-butyloxycarbonyl
Bn=benzyl
t-Bu=t-butyl
n-BuLi=butyllithium
Cbz=benzyloxycarbonyl
DCC=dicyclohexylcarbodiimide
DMF=dimethylformamide
DMSO=dimethylsulfoxide
Et=ethyl
EtOAc=ethyl acetate
Et$_2$O=diethyl ether
EtOH=ethanol
FAB-MS=fast atom bombardment mass spectrum
FD-MS=field desorption mass spectrum
HPLC=High Performance Liquid Chromatography
HRMS=high resolution mass spectrum
HOBT=1-hydroxybenzotriazole hydrate
i-PrOH=isopropanol
IR=Infrared Spectrum
Me=methyl
MeOH=methanol
NMR=Nuclear Magnetic Resonance
RPHPLC=Reversed Phase High Performance Liquid Chromatography
SiO$_2$=silica gel
TEA=triethylamine
TFA=trifluoroacetic acid
THF=tetrahydrofuran
TLC=thin layer chromatography
Ts=tosyl (p-toluenesulfonyl)

Unless otherwise stated, pH adjustments and work up are with aqueous acid or base solutions.

The $R_f$ values in the examples are determined by silica gel thin layer chromatography (Kieselgel 60 F-254) in the following systems:

(A) Chloroform-Methanol-Acetic Acid 135:15:1
(B) Ethyl Acetate-Acetic Acid-Absolute Alcohol 90:10:10
(C) Ethyl Acetate-Hexanes 30:70

EXAMPLE 1

Preparation of (1R,4aR,8aR)-Perhydroisoquinolin-1-yl-carbonyl-N-[(1S)-4-[(aminoiminomethyl)amino]-1-(benzo-thiazol-2-ylcarbonyl)butyl]-L-prolinamide. 1.5 H$_2$SO$_4$

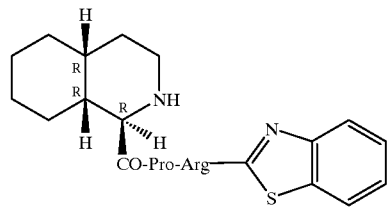

A. N-Methoxycarbonylphenethylamine

To a stirred solution of phenethylamine (75.2 mL, 0.6 mol) and triethylamine (83 mL, 0.6 mol) in THF (500 mL) was added slowly methyl chloroformate (46.2 mL, 0.6 mol) dissolved in THF (50 mL). After the reaction was stirred for an additional 1 h at room temperature, diethyl ether (2 L) and 1 N HCl (800 mL) was added. The organic layer was washed with water, dried (MgSO$_4$), and concentrated in vacuo to give a clear oil of pure title compound (102 g, 95%).

B. 2-Methoxycarbonyl-DL-1,2,3,4-tetrahydoisoquinoline-1-carboxylic acid

To a solution of N-methoxycarbonyl phenethylamine (102 g, 0.57 mol) in trifluoroacetic acid (300 mL) was added glyoxylic acid (63 g, 0.68 mol), and the mixture was heated to reflux temperature. After 4 h at reflux the reaction was cooled to room temperature, solvent removed in vacuo, and diethyl ether (800 mL)/water (100 mL) was added to the residue. The reaction mixture pH was raised to 12 with 5 N NaOH and the aqueous layer separated. To the aqueous layer was added diethyl ether (500 mL), and the solution was acidified to pH 2.5 with 5 N HCl. The organic layer was separated, dried (MgSO$_4$), filtered, and the filtrate was concentrated in vacuo to afford an oil of pure title compound (107 g, 80%); FAB-MS 236 (MH$^+$).

C. 2-Methoxycarbonyl-DL-1,2,3,4-tetrahydoisoquinoline-1-carboxylic acid t-butyl ester To a stirred, cooled (0° C.), solution of 2-methoxycarbonyl-DL-1,2,3,4-tetrahydoisoquinoline-1-carboxylic acid (105 g, 0.45 mol) in CH$_2$Cl$_2$ (200 mL) was added t-butanol (52 mL, 0.54 mol) and DCC (92 g, 0.45 mol). After 2 h at 0° C. and 24 h at room temperature the solvent was removed in vacuo, and ethyl acetate (800 mL)/1 N NaHCO$_3$ (300 mL) was added to the residue. The organic layer was separated, washed with water, 1.5 N citric acid, and water. The organic layer was dried (MgSO$_4$), filtered, and the filtrate was concentrated in vacuo to afford an oil of pure title compound (106 g, 81%); FAB-MS 292 (MH$^+$); TLC R$_f$(A) 0.61; elemental analysis (calcd) C$_{16}$H$_{21}$NO$_4$: C, 65.96; H, 7.27; N, 4.81; Found: C, 66.24, H, 7.28, N, 4.73.

D. 2-methoxycarbonyl-(1RS,4aSR,8aSR)-perhydroisoquinoline-1-carboxylic acid t-butyl ester A solution of 2-methoxycarbonyl-DL-1,2,3,4-tetrahydro-isoquinoline-1-carboxylic acid t-butyl ester (105 g, 0.36 mol) in t-butanol (800 mL) was reduced over 5% Rh/Al$_2$O$_3$ (52.5 g) at 55 bar (800 psi) of hydrogen in a high pressure apparatus at 50° C. for 24 hours. The reaction mixture was filtered through a pad of diatomaceous earth, and the filtrate was concentrated in vacuo. The resulting oil was dried to give pure title compound (96.5 g, 90%); FD-MS 298 (MH$^+$); TLC R$_f$ (C) 0.63.

E. 2-Methoxycarbonyl-(1RS,4aRS,8aRS)-perhydroisoquinoline-1-carboxylic acid ethyl ester To a solution of 2-methoxycarbonyl-(1RS,4aSR,8aSR)-perhydroisoquinoline-1-carboxylic acid t-butyl ester (81.2 g, 273 mmol) in EtOH (500 mL) was added sodium ethoxide (21% in ethanol) (88.4 mL, 273 mmol) and the reaction mixture was refluxed (24 h). The organic solvent was evaporated in vacuo, ethyl acetate (400 mL) and water (100 mL) was added to the residue. The organic layer was separated, washed twice with water, dried (MgSO$_4$), filtered, and the filtrate was concentrated in vacuo to afford an oil of pure title compound (70 g,.95%); FAB-MS 270 (MH$^+$); TLC R$_f$ (A) 0.61.

F. 2-Methoxycarbonyl-(1RS,4aRS,8aRS)-perhydroisoquinoline-1-carboxylic acid

To a solution of the product of step E (70 g, 260 mmol) in THF (250 mL) was added 2 N NaOH (156 mL, 312 mmol) and the reaction mixture stirred at room temperature (30 h). The organic solvent was evaporated in vacuo, diethyl ether (400 mL) and water (100 mL) was added to the residue. The aqueous layer separated and ethyl acetate (400 mL) was added. The pH of the solution was adjusted to 2.0 with 5 N HCl. The organic layer was dried (MgSO$_4$), filtered, and the filtrate was concentrated in vacuo to give a clear oil. The oil was crystallized from hexane (200 mL) to afford pure title compound (46.4 g,.74%); FAB-MS 242 (MH$^+$); TLC R$_f$ (A) 0.36; elemental analysis (calcd) C$_{12}$H$_{19}$NO$_4$: C, 59.74; H, 7.94; N, 5.81; Found: C, 59.95, H, 7.88, N, 5.54. NMR assignments were made by homonuclear decoupling, COSY, HMQC, and DEPT experiments.

G. 2-Cbz-(1RS,4aRS,8aRS)-perhydroisoquinoline-1-carboxylic acid

To a stirred solution of the product of step F (46 g, 191 mmol), at room temperature, in anhydrous CH$_3$CN (200 mL) under an inert atmosphere was added a solution of iodotrimethylsilane (62.4 mL, 440 mmol) in CH$_3$CN (60 mL). The reaction mixture was stirred at 55° C. for 30 min and cooled to room temperature. The reaction was quenched with water (100 mL) followed by sodium metabisulfite (1 g). The pH of the reaction was raised to 10.0 with 5 N NaOH, and benzyl chloroformate (27.3 mL, 191 mmol) was added dropwise while the pH maintained at 10 with 2 N NaOH. After the reaction was stirred for an additional 30 min at room temperature, the organic solvent was evaporated in vacuo, and diethyl ether (200 mL) was added. The reaction was allowed to stand at room temperature (2 h) and ethyl acetate (200 mL) was added. The aqueous solution was acidified to pH 2.5 with 5 N HCl; the organic layer was separated, dried (MgSO$_4$), filtered, and the filtrate was concentrated in vacuo to give pure title compound as an oil (39.5 g, 65%); FAB-MS 318 (MH$^+$); elemental analysis (calcd) C$_{18}$H$_{23}$NO$_4$: C, 68.12; H, 7.30; N, 4.41; Found: C, 66.37, H, 7.52, N, 4.37.

H. 2-Cbz-(1RS,4aRS,8aRS)-perhydroisoquinoline-1-carbonyl-Pro-O-t-Bu

To a stirred, cooled (0° C.) solution of the product of step G (39 g, 123 mmol) in DMF (200 mL) was added proline t-butyl ester (21.1 g, 123 mmol), 1-hydroxybenzotriazole (16.6 g, 123 mmol), and DCC (25.3 g, 123 mmol). The reaction mixture was stirred for 2 h at 0° C. and 24 h at room temperature. The reaction precipitate was filtered and the filtrate concentrated in vacuo to an oil. The oil was dissolved in EtOAc (200 mL) and water (100 mL). The organic layer was washed sequentially with 1 N NaHCO$_3$, water, 1.5 N citric acid, and water. The organic layer was dried (MgSO$_4$), filtered, and the filtrate evaporated to an amorphous solid of the title compound as a mixture of diastereomers (52.7 g, 91%) FAB-MS 471 (MH$^+$).

I. 2-Cbz-(4aR,8aR)-perhydroisoquinoline-1(R)-carbonyl-Pro-OH

To a stirred solution of the product of step H (52.4 g, 111 mmol) in CH$_2$Cl$_2$ (20 mL) was added trifluoroacetic acid (70 mL) and anisole (5 mL). The reaction mixture was stirred at room temperature for 1 h and concentrated in vacuo without heating. The residue was diluted with diethyl ether (400 mL), water (100 mL), and the pH of the solution was adjusted to 10.0 with 5 N NaOH. The aqueous layer separated and ethyl acetate (300 mL) was added. The pH of the solution was adjusted to 2.5 with 5 N HCl; the organic layer was separated, dried (MgSO$_4$), filtered, and the filtrate was concentrated in vacuo to give a clear oil. The oil was dissolved in diethyl ether (500 mL) and (L)-(−)-alpha-methylbenzylamine was added to the solution. The solution was allowed to stand at room temperature (24 h). The resulting solid was filtered, washed with diethyl ether and dried. The solid was suspended in ethyl acetate, washed with 1.5 N citric acid, and water. The organic layer was dried (MgSO$_4$), filtered, and the filtrate evaporated to give the title compound as an oil (20.2 g, 44%). FAB-MS 415 (MH$^+$); [a]D=3.2° (C=0.5, MeOH); elemental analysis (calcd) C$_{23}$H$_{30}$N$_2$O$_5$: C, 66.65; H, 7.30; N, 6.76. Found: C, 66.38, H, 7.36, N, 6.63.

J. Boc-Arg(Tosyl)-N(OMe)Me

To a stirred, cooled (0° C.) solution of Boc-L-Arg(Tosyl)-OH (34.2 g, 79.8 mmol) in DMF (150 mL) was added N,O-dimethylhydroxylamine hydrochloride (15.6 g, 159.6 mmol) followed by diisopropylethylamine (27.8 mL, 159.6 mmol), HOBT (10.8 g, 79.8 mmol), and DCC (16.5 g, 79.8 mmol). The reaction mixture was stirred for h at 0° C. and warmed to room temperature and stirred 18 h. The reaction mixture was cooled (0° C.), the precipitate filtered, and the mother liquor concentrated to dryness in vacuo. The resulting oil was dissolved in EtOAc and was washed sequentially with 1 N NaHCO$_3$, water, 1.5 N citric acid, and water. The organic solution was dried (MgSO$_4$), and evaporated to dryness in vacuo. The resulting oil was dissolved in EtOAc; and, after standing at 4° C. (4 h), the precipitate was filtered, washed with EtOAc and dried to give pure title compound (21.2 g, 57%). FAB-MS 472 (MH$^+$); Anal. Calcd. for C$_{20}$H$_{33}$N$_5$O$_6$S: C, 50.94; H, 7.05; N, 14.85. Found: C, 52.29; H, 7.32; N, 14.98.

K. 2-[Boc-Arg(Tosyl)]benzothiazole

To a stirred, cooled (−78° C.), solution of anhydrous THF (150 mL) was added 1.6 M n-butyllithium in hexane (150 mL, 240 mmol) under an inert atmosphere. To the reaction mixture was slowly added a solution of benzothiazole (32.4 g, 240 mmol) in THF (150 mL). After addition, a solution of the amide of step J (22.6 g, 48 mmol) in DMSO (27 mL) was added slowly to the reaction mixture. The reaction mixture was stirred at −78° C. for 3 h and for 40 min with an ice bath. The reaction mixture was diluted with 1.5 N citric acid (300 mL) slowly. The resulting mixture was concentrated in vacuo to approximately 400 mL before EtOAc (200 mL) and water (100 mL) were added. The organic layer was washed 3×with water, dried (MgSO$_4$), and evaporated in vacuo to give an oil. The crude oil was purified by chromatography on silica gel using a step gradient elution (CHCl$_3$100 to EtOAc 100) to yield pure ketone (17.4 g, 66%). FAB-MS 546 (MH$^+$); [α]D=25.8° (C, 0.5 CHCl$_3$); elemental analysis (calcd) C$_{25}$H$_{31}$N$_5$O$_5$S: C, 55.03; H, 5.73; N, 12.83. Found: C, 54.73, H, 5.72, N, 12.69.

L. 2-[Boc-Arg(Tosyl)(OH)]benzothiazole

To a stirred, cooled (0° C.) solution of the ketone of Part K (2.7 g, 4.95 mmol) in EtOH (60 mL) was added sodium borohydride (187 mg, 4.95 mmol). The reaction mixture was stirred at 0° C. for 1 h and slowly warmed to room temperature overnight. The mixture's pH was adjusted to 2.0 with 2 N HCl and then raised to pH 7.0 with 1 N NaOH. The resulting mixture was diluted with EtOAc (200 mL) and water (100 mL). The organic layer was dried (MgSO$_4$), and evaporated to give the crude alcohol (2.7 g, 99%). FAB-MS 548 (MH$^+$); TLC R$_f$ (A) 0.21.

M. Benzyloxycarbonyl-(1R,4aR,8aR)-perhydroisoquinolin-1-ylcarbonyl-N-[(1S)-4[(N-tosylaminoiminomethyl)amino]-1-[(benzothiazol-2-yl)(hydroxy)methyl]butyl]-L-prolinamide To a flask containing the alcohol of step L (2.6 g, 4.75 mmol) was added anisole (5 mL), followed by trifluoroacetic acid (70 mL). The reaction mixture was stirred at 0° C. for 20 min and concentrated in vacuo without heating. The reaction mixture was diluted with diethyl ether (400 mL), and the solid was filtered and dried to give 2.3 grams of crude 2-[H-Arg(Tosyl)(OH)]benzothiazole.

In flask 1 the product of step I (1.97 g, 4.75 mmole) was dissolved in CH$_2$Cl$_2$ (50 mL), cooled to −15° C., and N-methylmorpholine (0.52 mL, 4.75 mmole) was added, followed by isobutyl chloroformate (0.62 mL, 4.75 mmole). The reaction mixture was stirred at −15° C. for 2 min.

In flask 2 the above crude 2-[H-Arg(Tosyl)(OH)]-benzothiazole (2.3 g, 4.74 mmole) was dissolved in CH$_2$Cl$_2$ (20 mL), cooled to 0° C., and diisopropylethylamine (2.5 mL, 14.3 mmole) was added to the solution. The reaction mixture was stirred at 0° C. for 2 min.

The contents of flask 2 was added to flask 1, and the reaction mixture was stirred for 2 h (−15° C.) followed by 24 h at room temperature. To the reaction mixture was added 1 N NaHCO$_3$ (1 mL) and the reaction solvent was removed in vacuo to afford an oil. The residue was dissolved in EtOAc (200 mL) and washed sequentially with 1.5 N citric acid, water, 1 N NaHCO$_3$ (100 mL), and water. The organic solution was dried (MgSO$_4$), and concentrated to dryness in vacuo to give the title alcohol.(9.0 g, 39%) as a crude solid. FAB-MS 844 (MH$^+$); TLC R$_f$ (A) 0.34.

N. Benzyloxycarbonyl-(1R,4aR,8aR)-perhydro-isoquinolin-1-ylcarbonyl-N-[(1S)-4-[(aminoiminomethyl)-amino]-1-[(benzothiazol-2-ylcarbonyl)butyl]-L-prolinamide A 500 mL three necked flask, equipped with a magnetic stirring bar and a thermometer, and under nitrogen, was charged with a solution of oxalyl chloride (0.74 mL, 8.4 mmol) in 10 mL of anhydrous CH$_2$Cl$_2$ and placed in a dry ice-acetone bath (−55° C. internal temperature). A solution of DMSO (1.2 mL, 17 mmol) in 200 mL of CH$_2$Cl$_2$ was added at a rate to keep the internal temperature at −55° C. Stirring was continued for 5 minutes and a solution of the alcohol of step M (1.4 g, 1.66 mmol) in 10 mL CH$_2$Cl$_2$ was added in one portion. The mixture was allowed to warm to −10° C. and stirred for 40 minutes. The solution was cooled (−55° C.), triethylamine (3.9 mL, 28 mmol) was added slowly, and, after addition, the cooling bath removed. When the temperature reached −20° C. a 1.5 N citric acid solution was added to the reaction. The organic layer was separated, washed once with water, dried (MgSO$_4$), and concentrated to dryness in vacuo to give the title protected ketone (1.4 g, 100%). FAB MS m/z 842 (MH$^+$); elemental analysis (calcd) C$_{43}$H$_{51}$N$_7$O$_7$S$_2$: C, 61.34; H, 6.10; N, 11.64. Found: C, 61.66, H, 6.58, N, 10.52.

O. (1R,4aR,8aR)-Perhydroisoquinolin-1-ylcarbonyl-N-[(1S)-4-[(aminoiminomethyl)amino]-1-(benzothiazol-2-ylcarbonyl)-butyl]-L-prolinamide. 1.5 H$_2$SO$_4$ The reaction flask of a HF-Reaction apparatus was charged with the protected ketone of step N (1.35 g, 1.60 mmol) and applied to HF deprotection of all protecting groups. After treating the peptide with 10 mL HF containing 1.0 mL of anisole and 1.0 mL dimethylsulfide for 1 h at 0° C., the HF was evaporated. The residue was treated with diethyl ether, and the precipitate was filtered and dried to a white solid. The solid (0.9 g) was dissolved in 0.01% H$_2$SO$_4$ and applied to a 5×25 cm of column Vydac C$_{18}$ resin. A gradient of increasing concentrations of CH$_3$CN (2% to 35%) was used to elute the peptide from the column. Fractions were collected and pooled on the basis of analytical RP-HPLC profile. The combined fractions were adjusted to pH 4.2 using AG1-X8 resin (Bio-Rad analytical anion exchange resin 50–100 mesh) in hydroxide form. The solution was filtered, and the filtrate was lyophilized to afford pure title compound (0.403 g, 36%). FAB-MS 554 (MH$^+$); elemental analysis (calcd) C$_{28}$H$_{39}$N$_7$O$_3$S. 1.5H$_2$SO$_4$: C, 47.99; H, 6.04; N, 13.99. Found: C, 48.02, H, 6.02, N, 13.33.

Examination of the above compound by RPHPLC (C$_{18}$ resin, gradient elution, 5–45% acetonitrile containing 0.1% TFA —water containing 0.1% TFA) revealed the product to be a mixture of about 95:5 S:R-isomers at the Arg center. This compound may be denoted as L-Arg-Ia for convenience.

(1R,4aR,8aR)-Perhydroisoquinolin-1-ylcarbonyl-N-[(1RS)-4-[(aminoiminomethyl)amino]-1-(benzothiazol-2-ylcarbonyl)-butyl]-L-prolinamide. 1.5 H$_2$SO$_4$ In a different preparation of this compound, in which a larger excess of the 2-benzothiazolyllithium reagent was used in the step corresponding to step K, above, a final product was obtained with an S:R-isomer ratio of about 1:1 as measured by RPHPLC and $^{13}$C NMR. This compound may be denoted as DL-Arg-Ia for convenience.

EXAMPLE 2

Preparation of (1R,4aS,8aS)-Perhydroisoquinolin-1-yl-carbonyl-N-[(1S)-4-[(aminoiminomethyl)amino]-1-(benzo-thiazol-2-ylcarbonyl)butyl]-L-prolinamide. $H_2SO_4$

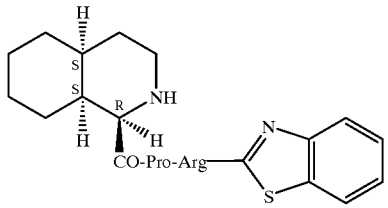

(I.e., insert the missing nitrogen atom in the perhydroisoquinoline ring.)

Using the isomeric 2-Cbz-(4aS,8aS)-perhydroisoquinoline-1(R)-carbonyl-Pro-OH and procedures similar to those described above, the title compound was obtained. FAB-MS 554 (MH+); elemental analysis (calcd) $C_{28}H_{39}N_7O_3S \cdot H_2SO_4 \cdot H_2O$: C, 50.21; H, 6.47; N, 14.64. Found: C, 50.12, H, 6.06, N, 14.42; [a]D=−69.60° (C, 0.5 MeOH).

What is claimed is:

1. A compound of formula I

Y—CO—X—CO—Arg—R    I wherein

Arg is L-arginyl;

R is 2-benzothiazolyl;

X—CO— is L-prolyl or (S)-azetidin-2-carbonyl; and

Y—CO— is a group of formula IIa, IIb, IIc or IId;

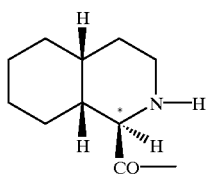    IIa

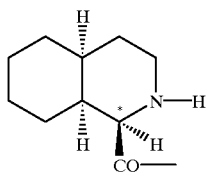    IIb

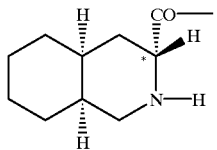    IIc

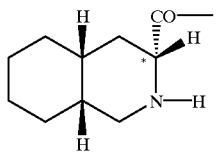    IId or a pharmaceutically acceptable salt thereof.

2. The compound (or salt thereof) of claim 1 in which X—CO— is L-prolyl (Pro).

3. The compound (or salt thereof) of claim 2 in which X—CO— is Pro and Y—CO— is a group of formula IIa or IIb.

4. The compound (or salt thereof) of claim 3 in which X—CO— is Pro and Y—CO— is a group of formula IIa.

5. The compound (or salt thereof) of claim 3 in which X—CO— is Pro and Y—CO— is a group of formula IIb.

6. The compound (or salt thereof) of any one of claims 1–5 wherein the chiral center indicated by the asterisk in the group Y is of (R)-stereochemistry corresponding to that of a D-amino acid.

7. The compound as claimed in claim 1 which is (1R, 4aR,8aR)-perhydroisoquinolin-1-ylcarbonyl-N-[(1S)-4-[(aminoiminomethyl)amino]-1-(benzothiazol-2-ylcarbonyl)-butyl]-L-prolinamide, or a pharmaceutically acceptable salt thereof.

8. The compound as claimed in claim 1 which is (1R, 4aR,8aR)-perhydroisoquinolin-1-ylcarbonyl-N-[(1RS)-4-[(aminoiminomethyl)amino]-1-(benzothiazol-2-ylcarbonyl)-butyl]-L-prolinamide, or a pharmaceutically acceptable salt thereof.

9. The salt as claimed in claim 7 or 8 which is the acid addition salt with sulfuric acid.

10. A pharmaceutical composition comprising a compound of formula I as claimed in claim 1, or a pharmaceutically acceptable salt thereof, in association with a pharmaceutically acceptable carrier, diluent or excipient.

11. A process for preparing a compound of formula I (or a pharmaceutically acceptable salt thereof) as provided in claim 1 which is oxidation of the alcohol of a corresponding compound of formula III Y—CO—X—CO—Arg(OH)—R    III in which Arg(OH) indicates that the carbonyl portion of the L-arginyl group is replaced by a hydroxymethylene group;

whereafter, when a functional group is protected using a protecting group, removing the protecting group; and whereafter, when a pharmaceutically acceptable salt of a compound of formula I is required, it is obtained by reacting the basic form of the compound of formula I with an acid affording a physiologically acceptable counterion or by any other conventional procedure; and wherein Arg, R, X and Y are defined as in claim 1.

12. An alcohol of formula III

Y—CO—X—CO—Arg(OH)—R    III in which

Arg is L-arginyl;

R is 2-benzothiazolyl;

X—CO— is L-prolyl or (S)-azetidin-2-carbonyl; and

Y—CO— is a group of formula IIa, IIb, IIc or IId;

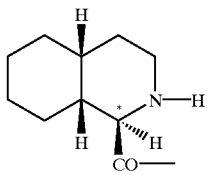    IIa

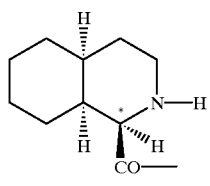
IIb
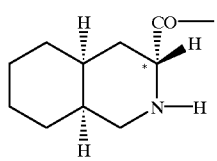
IIc
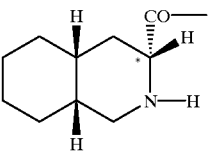
IId
and Arg(OH) indicates that the carbonyl portion of the L-arginyl group is replaced by a hydroxymethylene group.
13. A method of inhibiting thrombosis in a mammal comprising administering to a mammal in need of treatment, an antithrombotic dose of a compound of formula I as claimed in claim 1.
* * * * *